United States Patent
Lewis

(10) Patent No.: US 10,234,382 B2
(45) Date of Patent: Mar. 19, 2019

(54) METHOD FOR DIAGNOSING LUNG DISEASES

(71) Applicant: PULMONIR LIMITED, Singleton Park, Swansea (GB)

(72) Inventor: Paul Lewis, Swansea (GB)

(73) Assignee: PULMONIR LIMITED, Swansea (GB)

(*) Notice: Subject to any disclaimer, the term of this patent is extended or adjusted under 35 U.S.C. 154(b) by 158 days.

(21) Appl. No.: 15/215,744

(22) Filed: Jul. 21, 2016

(65) Prior Publication Data

US 2016/0327477 A1 Nov. 10, 2016

Related U.S. Application Data

(63) Continuation-in-part of application No. PCT/GB2015/000007, filed on Jan. 13, 2015.

(51) Int. Cl.
*G01N 21/3577* (2014.01)
*G01N 33/68* (2006.01)
*G01N 21/35* (2014.01)
*G01N 33/48* (2006.01)

(52) U.S. Cl.
CPC ......... *G01N 21/3577* (2013.01); *G01N 21/35* (2013.01); *G01N 33/6893* (2013.01); *G01N 33/48* (2013.01); *G01N 2021/3595* (2013.01); *G01N 2333/4725* (2013.01); *G01N 2400/40* (2013.01); *G01N 2800/122* (2013.01)

(58) Field of Classification Search
CPC ........... G01N 2021/3595; G01N 21/35; G01N 21/3577; G01N 2333/4725; G01N 2800/122; G01N 33/48; G01N 33/487; G01N 33/68; G01N 33/6893; G01N 2800/40; Y10T 436/143333; Y10T 436/173845

USPC ............ 436/63, 87, 94, 111, 164, 171; 422/82.05, 82.09

See application file for complete search history.

(56) References Cited

U.S. PATENT DOCUMENTS

2008/0241954 A1 10/2008 Spiteri
2010/0129926 A1* 5/2010 Spiteri ................. G01N 21/35
 436/171

FOREIGN PATENT DOCUMENTS

WO 2012/001370 * 1/2012

OTHER PUBLICATIONS

Lewis et al. BMC Cancer, vol. 10:640, 2010, pp. 1-10.*
Written Opinion of the International Search Authority and International Search Report dated May 8, 2015.
Whiteman, S.C. et al., FTIR spectroscopic analysis of sputum: Preliminary findings on a potential novel diagnostic marker for COPD. Therapeutic Advances in Respiratory Disease, Sage, London, vol. 2 COPD, No. 1, Jan. 1, 2008 pp. 23-31.
N. Patel, et al., FTIR Spectroscopic profiling of COPD sputum: identification of distinct spectral signatures and correlation to COPD status. THORAX 2010, vol. 65, No. Suppl. 4, Nov. 16, 2010, pp. A124-A125.
Lewis, A.T., et al. Detection of Lewis antigen structural change by FTIR spectroscopy, Carbohydrate Polymers. Applied Science Publishers, Ltd., Barking. GB. vol. 92, No. 2. Oct. 6, 2012, pp. 1294-1301.

* cited by examiner

*Primary Examiner* — Maureen Wallenhorst
(74) *Attorney, Agent, or Firm* — King & Schickli, PLLC

(57) ABSTRACT

A method and kit are provided for diagnosing and monitoring the progress of COPD using FTIR spectral analysis of sputum samples where spectral data is obtained and used to monitor the progression of the disease over time.

12 Claims, 2 Drawing Sheets

METHOD FOR DIAGNOSING LUNG DISEASES

This application is a continuation-in-part of international patent application no. PCT/GB2015/000007 filed on Jan. 13, 2015 which in turn claims priority from British Patent Application No. 1401055.7 filed on Jan. 22, 2014, the disclosures of which are incorporated herein by reference in their entirety.

TECHNICAL FIELD

The present application relates to methods for diagnosing lung diseases and in particular chronic obstructive pulmonary disease (COPD). The invention relates in particular to methods for detecting the progression of COPD in an individual and the risk of flair ups in the condition.

BACKGROUND

COPD is a common, progressively disabling disease and a major health burden worldwide. The disease is a disabling and complex disease and a major public health problem worldwide as it affects an estimated 600 million people and ranks within the top 5 leading causes of death. The disease is characterised by partially reversible airflow obstruction driven by in situ inflammatory changes and airway wall remodelling. Consequently COPD patients have a poor quality of life, aggravated by acute distressing flare-ups. These infective/inflammatory exacerbations increase with disease severity, occurring on a background of variable but progressive natural decline in the patient's lung function.

Currently COPD is measured at particular points in time and this gives an indication of the disease state at that point. There is currently no routine near-patient sensitive tools to monitor COPD, and more specifically how to predict, which COPD patients are more prone to rapid deterioration in lung function and to increased exacerbations. COPD 'flare-ups' are diagnosed usually on clinical grounds; including a deterioration in specific symptoms (e.g. shortness of breath). Currently measurements of a patient's condition are made using forced expiratory volume in one second (FEV) measurements following bronchodilation, but these measurements are not predictive of disease progression or outcome. Assessment of COPD has been made by bronchial/lung biopsies and bronchoalveolar lavage but whilst greatly advancing knowledge of COPD status, such measures are not amenable to everyday use. Spontaneous and induced sputum analysis has also been performed using a mix of biological technologies and recent progress with exhaled breath analysis looks promising but is limited by high magnitude inter-patient differences in exhaled volatile organic compounds and nitric oxide markers, very low levels of which are not easily detected, so potentially reducing routine clinical value of this biomarker. Thus current methods are in early stage research or at the preclinical trial stage or just not amenable to clinical so leaving a clinical need and challenge to identify patients with COPD in an effective, practical and non-invasive way to enable determination and monitoring of disease status with sufficient sensitivity to give early warnings of exacerbations of the disease.

Fourier transform infrared spectroscopy (FTIR) is a non-invasive technology that can detect structural changes in molecules from tissue or cells. Such changes can be visualized using a spectrum of wave numbers usually taken from the mid infrared range (4000 to 400 $cm^{-1}$). FTIR has shown promise as a sensitive diagnostic tool to distinguish neoplastic from normal cells in cancers such as colon cancer, prostate, breast, cervical, gastric, oral and oesophageal cancer. In these and other studies, biochemical changes are often observed between tumour and normal cells within a wavenumber range known as the "fingerprint region" (encompassing 1800 to 950 $cm^{-1}$). Whilst FTIR has proven applicability in other disciplines FTIR analysis has not been applied to address the clinical needs of COPD where spectral profiles of human sputum are made to identify differences between COPD and health.

The present invention seeks to overcome the problems that currently exist with monitoring COPD by providing an easy to use analysis process which can be used to analyse the stage of and progression of COPD so appropriate treatment can be provided for a patient according to their particular condition. Spectroscopy methods such as FTIR and variable filter infrared spectroscopy (VFIR) can be used.

SUMMARY

According to one aspect of the present invention, there is provided a method for diagnosing COPD in a subject or for identifying the progression of COPD in a subject, the method comprising:

(a) performing FTIR or VFIR spectral analysis of a sputum sample obtained from the subject;

(b) comparing the spectrum produced from the sample with an FTIR or VFIR spectrum from a normal control or for a spectrum previously taken for the subject, wherein a difference between the spectrum produced from the sample and the normal control or spectrum previously taken at one or more wavenumbers within one or more ranges selected from about 940 $cm^{-1}$ to about 970 $cm^{-1}$, about 1080 $cm^{-1}$ to about 1130 $cm^{-1}$, about 1230 $cm^{-1}$ to about 1250 $cm^{-1}$, about 1570 $cm^{-1}$ to about 1590 $cm^{-1}$, about 1620 $cm^{-1}$ to about 1650 $cm^{-1}$, and about 1720 $cm^{-1}$ to about 1750 $cm^{-1}$ is indicative of a subject suffering from COPD or the progression of COPD in a subject.

Remarkably, it has been found that the methods of the present invention are particularly effective at identifying the progression of COPD and in particular the risk of flair ups at an early stage.

Preferably, an increase or decrease in absorbance at the same wavenumber or a shift in position of absorbance between wavenumbers between sputum spectra of individuals with COPD and normal controls is selected within one or more ranges selected from about 940 $cm^{-1}$ to about 970 $cm^{-1}$, about 1080 $cm^{-1}$ to about 1130 $cm^{-1}$, about 1230 $cm^{-1}$ to about 1250 $cm^{-1}$, about 1570 $cm^{-1}$ to about 1590 $cm^{-1}$, about 1635 $cm^{-1}$ to about 1650 $cm^{-1}$, and about 1735 $cm^{-1}$ to about 1750 $cm^{-1}$ and which is indicative of subject suffering from COPD or the progression of COPD in a subject.

It is preferred that an increased absorbance at a wavenumber is selected from one or more of about 965 $cm^{-1}$, about 970 $cm^{-1}$, about 1125 $cm^{-1}$, about 1130 $cm^{-1}$, about 1235 to about 1248 $cm^{-1}$, about 1570 $cm^{-1}$ to about 1590 $cm^{-1}$, about 1640 $cm^{-1}$ to about 1648 $cm^{-1}$, and about 1740 $cm^{-1}$ to about 1748 $cm^{-1}$ in the sample when compared with the normal control is indicative of COPD in a subject.

In a preferred method of the first aspect of the invention, said method alternatively or further comprises in part b) comparing the said spectrum at wavenumbers within the range from about 1400-1420 $cm^{-1}$ wherein a difference between the spectrum produced from the sample and the normal control is indicative of subject suffering from COPD or the progression of COPD in a subject.

It is envisaged that the difference in wave number absorbance between COPD or high risk and normal is statistically significant, for example as determined by using a statistical test such as a "t-test".

According to another aspect of the present invention, there is provided a method for monitoring the progression of COPD in a subject, the method comprising:

(a) performing FTIR or VFIR spectral analysis of a sputum sample obtained from the subject;

(b) comparing the spectrum produced from the sample with an FTIR or VFIR spectrum from a normal control or for a spectrum previously taken for the subject, wherein a difference between the spectrum produced from the sample and the normal control or spectrum previously taken at one or more wavenumbers within one or more ranges selected from about 940 $cm^{-1}$ to about 970 $cm^{-1}$, about 1080 $cm^{-1}$ to about 1130 $cm^{-1}$, about 1230 $cm^{-1}$ to about 1250 $cm^{-1}$, about 1570 $cm^{-1}$ to about 1590 $cm^{-1}$ about 1620 $cm^{-1}$ to about 1650 $cm^{-1}$, and about 1720 $cm^{-1}$ to about 1750 $cm^{-1}$ is indicative of a subject suffering from COPD or the progression of COPD in a subject.

Preferably, an increase or decrease in absorbance at the same wavenumber or a shift in position of absorbance between wavenumbers between sputum spectra of individuals with COPD and normal controls is selected within one or more ranges selected from about 940 $cm^{-1}$ to about 970 $cm^{-1}$, about 1080 $cm^{-1}$ to about 1130 $cm^{-1}$, about 1230 $cm^{-1}$ to about 1250 $cm^{-1}$, about 1570 $cm^{-1}$ to about 1590 $cm^{-1}$, about 1635 $cm^{-1}$ to about 1650 $cm^{-1}$, and about 1735 $cm^{-1}$ to about 1750 $cm^{-1}$ and which is indicative of the progression of COPD in a subject suffering from COPD or the progression of COPD in a subject.

It is preferred that an increased absorbance at a wavenumber is selected from one or more of about 965 $cm^{-1}$, about 970 $cm^{-1}$, about 1080 $cm^{-1}$, about 1130 $cm^{-1}$, about 1235 to about 1248 $cm^{-1}$, about 1570 $cm^{-1}$ to about 1590 $cm^{-1}$, about 1640 $cm^{-1}$ to about 1648 $cm^{-1}$, and about 1740 $cm^{-1}$ to about 1748 $cm^{-1}$ in the sample when compared with the normal control is indicative of progression of COPD in a subject.

In a preferred method of the second aspect of the invention, said method alternatively or further comprises in part b) comparing the said spectrum at wavenumbers within the range from about 1400-1420 $cm^{-1}$ wherein a difference between the spectrum produced from the sample and the normal control is indicative of subject suffering from COPD or the progression of COPD in a subject.

Preferably the said method comprises or consists of comparing the spectrum at wavenumbers within the ranges comprising or consisting of:

about 1230 $cm^{-1}$ to about 1250 $cm^{-1}$, about 1570-1590 $cm^{-1}$, about 1720-1750 $cm^{-1}$ and about 1400-1420 $cm^{-1}$.

More preferably still, the said method comprises or consists of comparing the spectrum at wavenumbers within any combination of ranges selected from the group comprising:

about 1230 $cm^{-1}$ to about 1250 $cm^{-1}$, about 1570-1590 $cm^{-}$, about 1720-1750 $cm^{-1}$ and about 1400-1420 $cm^{-1}$.

Accordingly, the methods of the present invention can be used to detect the onset as well as the progression of COPD, and in particular, the risk of flair ups at an early stage.

In addition the method of the invention can be practised to identify acute exacerbation of COPD also known as acute exacerbations of chronic bronchitis (AECB) which is a sudden worsening of COPD symptoms (shortness of breath, quantity and color of phlegm) that typically lasts for several days.

Preferably, the control may be from the same subject from a previous sample, to thus monitor onset or progression. However, it is also preferred that the control may be normalised for a population, particularly a healthy or normal population, where there is no COPD.

It is preferred that at least two quantification steps are provided, spaced apart temporally. It is envisaged that the steps are spaced apart by a few days, weeks, years or months, to determine whether the difference between the spectra has changed, thus indicating whether there has been a change in the progression of the COPD, enabling comparisons to be made between the spectra performed on two or more occasions, as an increase in the difference over time is indicative of the onset or progression of the cancer, whereas a decrease may indicate decreased risk or a decrease in the progression of the cancer.

Preferably, the change in the difference between the spectra is statistically significant, for example as determined by using a "t-test".

The methods of the invention are particularly useful in detecting progression of COPD by analysing the sputum of a subject. As a result of the tests the prognosis and choice of treatment are dependent upon the condition identified as a particular point in time.

The methods of present invention may also be used for monitoring the efficacy of a treatment for COPD, for example by monitoring the change in the difference between the spectra from the normal control and the sample over the course of a treatment regime.

Sputum samples can be obtained by any number of means known in the art, such as will be apparent to the skilled person. It will be appreciated that sputum samples can be obtained without using invasive techniques.

According to another aspect of the present invention, there is provided a kit for use in a method as described herein, wherein the kit comprises an FTIR or VFIR machine and instructions for use in a method as described herein.

Preferably, the kit further comprises a collection means for collecting sputum samples. Suitable collection means will be apparent to the skilled person and could include, for example a suitable container such as a plastic bottle or cup preferably provided with a lid such as a screw-thread or push-on cap.

It is envisaged that the collection means comprises a lab on chip unit.

Preferably the kit includes a memory unit which is arranged such that patient information stored therein is associated with timing data relating to the time at which: the patient information is received; or the patient information is stored.

It is envisaged that the memory unit is arranged to store a plurality of determined disease states, and timing data relating to the time at which each determination was made.

It is preferred that the memory unit is arranged to store a plurality of pieces of patient information received over time from a patient.

Preferably the output unit is arranged to provide an output indicative of lung disease state according to the determination made by the processing unit, the output indicating the state as either stable or changing.

It is preferred that the output unit is arranged to provide an output indicative of the initiation of a COPD related disease response.

It is envisaged that the output unit is arranged to produce a local output to a local user, and/or is arranged to transmit information from the apparatus to a remote monitoring station.

Example embodiments of the present invention will now be described with reference to the accompanying figures.

DETAILED DESCRIPTION

Figure 1:
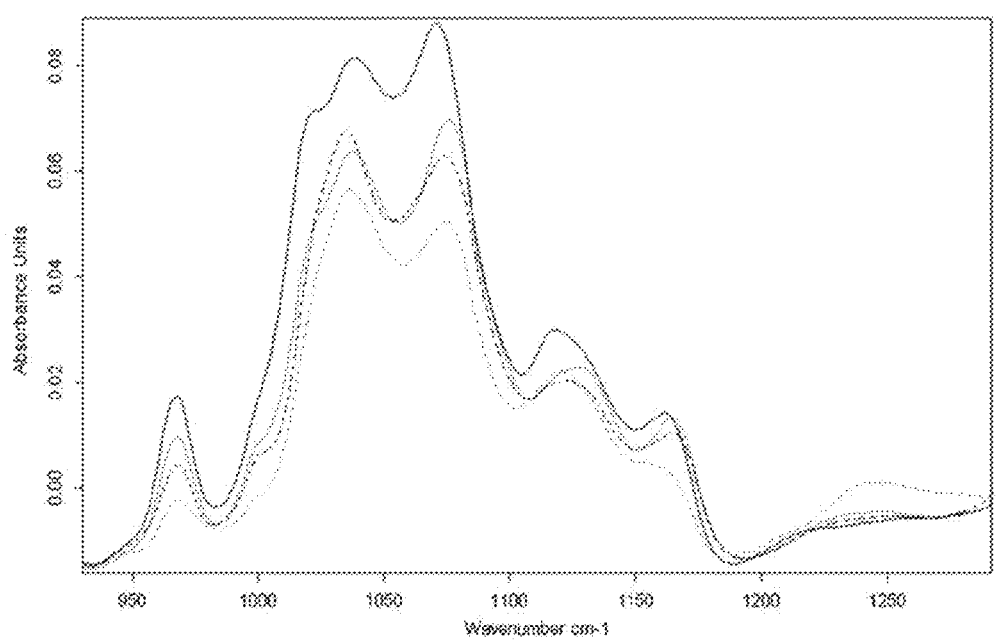
FIG. 1 shows a graph of certain peaks for COPD measurement.
Figure 2:
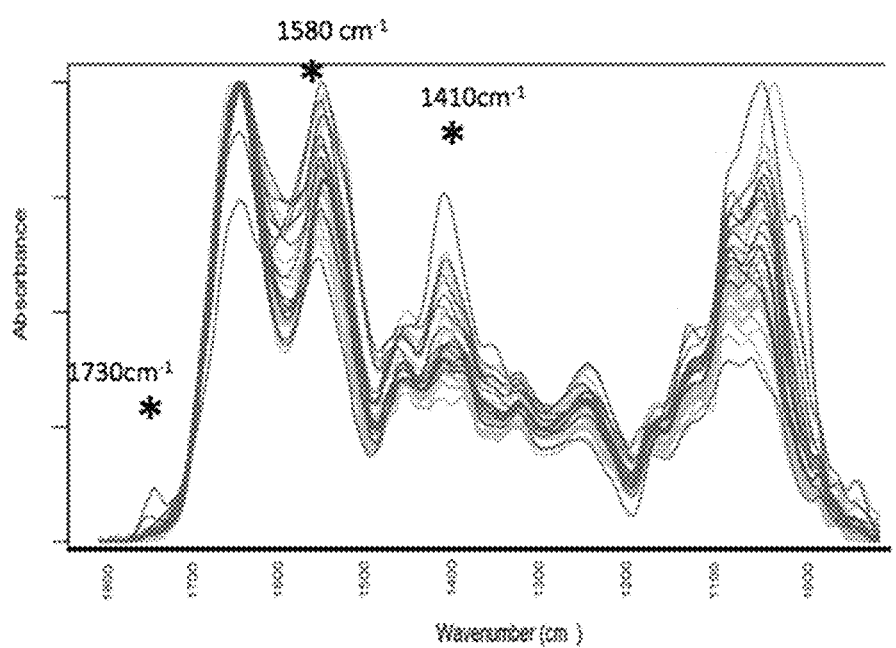
FIG. 2 shows further infrared wavenumber ranges (1570-1590 cm$^{-1}$, 1720-1750 cm$^{-1}$, 1400-1420 cm$^{-1}$) that provide predictive readings diagnostic for COPD exacerbation using FTIR technology, comparing patients who were COPD baseline at time of sampling (green lines/points) and patients who were COPD exacerbaters (red lines/points) (n=15 in both samples).

Within this specification embodiments have been described in a way which enables a clear and concise specification to be written, but it is intended and will be appreciated that embodiments may be variously combined or separated without parting from the invention. In this specification, the terms "comprises" and "comprising" are interpreted to mean "includes, among other things". These terms are not intended to be construed as "consists of only". Further, within this specification, the term "about" means plus or minus 20%, more preferably plus or minus 10%, even more preferably plus or minus 5%, most preferably plus or minus 2%. For example, it will be appreciated that there may be slight variation, for example ±5 cm$^{-1}$, in the position of a specific wavenumber absorbance between FTIR or VFIR technologies due in part to differing resolution.

As used herein, the term "subject" refers to an animal, preferably a mammal and in particular a human. In a particular embodiment, the subject is a mammal, in particular a human, who is suffering from, is suspected of suffering from or is at risk of suffering from lung cancer. The term "diagnosis" encompasses identification, confirmation, and or characterisation of the presence or absence of lung cancer, together with the developmental stage thereof, such as early stage or late stage, or benign or metastatic cancer. Further, the term "normal control" means a sample which is representative of the presence of no COPD and not suspected as being high risk for COPD. For example, the normal control may be a sample obtained from a subject who is not suffering from COPD.

Materials and Methods

Fourier transform infrared spectroscopy/Variable Filter Infrared spectroscopy IR spectra were obtained with a Bruker Alpha Fourier Transform IR (FTIR) instrument equipped with a platinum ATR single reflection diamond sampling module (Bruker Optics). Samples were spotted directly onto the sampling module and left to air-dry at room temperature prior to spectral acquisition. Data points were collected as an average of 24 scans per sample between the wave number range of 450-4000 cm-1 at a resolution of 4 cm-1, controlled by Optics User Software (OPUS) version 6.5 (Bruker Optics). The process was repeated until six replicates were generated per sample. The resulting spectra were background corrected and smoothed using a nine-point Savitzky-Golay algorithm. Peak positions were determined using OPUS version 6.5 (Bruker Optics). The same process was carried out using a variable filter infrared spectroscopy instrument.

FTIR/VFIR Analysis

IR spectra were generated for fucose, galactose, mannose, Nacetylglucosamine, N-acetylgalactosamine, sialic acid, Lex, Ley, Lea and Leb, sialyl-Lex and sulfo-Lex. Sugar films were obtained for analysis by preparing a solution of sugar in Milli-Q water at a concentration of 1 mg ml$^{-1}$. 3 µl of sugar solution was placed on the FTIR sampling module or the VFIR sampling module for spectral acquisition. Lewis antigen spectra were generated at a concentration of 5 mg ml$^{-1}$ following identical methodology.

Sputum FTIR/VFIR Analysis

Spontaneous sputum was collected from a patient with COPD who was an ex-smoker with no symptoms for any other respiratory disease and not experiencing an exacerbation at the time of sputum collection. Therefore, the patient was considered representative of stable COPD with baseline characteristics and no bacterial or viral infection. Additionally, samples were also analysed from patients who were COPD exacerbaters. Informed consent to provide a sputum sample was obtained. 3 µl of raw sputum was placed onto the FTIR or the VFIR sampling module for spectral acquisition. IR absorbance peak positions within the COPD spectrum were compared to those within published representative spectra of COPD and normal sputa results.

IR Spectra of Monosaccharides Found in Mucin Glycans

Infrared absorption spectra were generated for the monosaccharide building blocks found in mucin glycan cores. All spectra were deemed highly reproducible through repetition of the procedure using repeated samples. Firstly, IR spectra were generated for mannose, fucose and galactose monosaccharides to establish the absorbance peak positions and intensities of each carbohydrate structure. Spectra are reported within the range of 900-1280 cm-1 as it is within this region that the maximum IR absorbance due to the presence of carbohydrates is noted to occur. Within this region, the following unique peaks associated with each monosaccharide were observed: mannose at 956 cm-1, 971 cm-1, 1020 cm-1, 1047 cm-1, 1167 cm-1, 1251 cm-1; fucose peaks at 963 cm-1, 996 cm-1, 1027 cm-1, 1057 cm-1, 1095 cm-1, 1131 cm-1, 1164 cm-1, 1216 cm-1 and galactose peaks at 1037 cm-1, 1068 cm-1, 1143 cm-1, 1249 cm-1. IR spectra was generated for sugar derivatives, including N-acetylglucosamine, N-acetylgalactosamine and sialic acid. These monosaccharides also present a unique IR absorption pattern in the carbohydrate region of the spectrum, with distinguishable major peaks (FIG. 1): sialic acid absorption peaks occur at 1024 cm-1, 1068 cm-1, 1125 cm-1, 1142 cm-1, 1210 cm-1, 1238 cm-1; GalNAc peaks at 976 cm-1, 1038 cm-1, 1076 cm-1, 1095 cm-1, 1115 cm-1, 1153 cm-1, 1219 cm-1 and GlcNAc peaks at 961 cm-1, 1025 cm-1, 1079 cm-1, 1103 cm-1.

Infrared absorption spectra were also generated for the components of mucin within the 1570-1590 cm$^{-1}$, 1720-1750 cm$^{-1}$ and 1400-1420 cm$^{-1}$ ranges.

IR Spectra of Lewis Antigens and Modified Derivatives

In comparing the absorption spectra for the Lewis antigens within the carbohydrate associated region of the spectra it can be seen that peak position and associated absorbance levels are extremely similar, which is to be expected based on their monosaccharide compositions. Major shared peaks occur at 968 cm-1, 1033 cm-1, and 1074 cm-1. However, low-frequency vibrations attributed to glycosidic linkages also contribute to the spectra. The Lewis b and y antigens both contain a second fucose residue in an α-2 glycosidic linkage to galactose which may account for a wavenumber shift at peaks around 1164 cm-1. Furthermore, fucose residues linked to GlcNAc via an α-3 linkage could account for the unresolved peak at around 1020 cm-1, prominent in the Lewis x (Lex) spectrum, present in the Lewis y spectrum but absent in both Lewis a and b.

The FTIR or VFIR spectra provides information on vibrations of chemical groups, this study has shown that it is possible to differentiate carbohydrates based on their infrared absorption peaks. We have identified a number of discrete sugar and sulphate associated infrared absorption peaks that can be used to predict the presence of the major mucin linked carbohydrates and mucin modifications observed in the IR spectrum of sputum. Analysis has shown that infrared spectroscopy is sugar specific and is able to discriminate between sugar moieties based on molecular bond vibrations. Polysaccharide spectra are also molecule-specific and not only contain peaks relating to monosaccharide components but also peaks inferring information on glycosidic linkage, providing details of carbohydrate conformation.

Unique absorption patterns due to composite vibrations of the sugar ring, CH wagging and OH flexing vibrations also occur in this region resulting in the formation of sugar-specific peaks in the spectra. The invention demonstrates that in patients suffering with COPD, diseased sputum shows changes in the carbohydrate associated region of FTIR/VFIR spectra arising from changes in sputum composition, which contains mainly mucins. The fact that FTIR/VFIR is able to distinguish between unmodified, sulphated and sialylated Lewis antigens and show variable antigen-specific IR peaks in disease sputum potentially makes it a powerful tool in glycoprotein analysis and can be used in the development of new technologies and methods for disease detection and monitoring using non-invasive techniques.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications are covered by the appended claims. The content of all references referred to herein are incorporated herein by reference in their entirety.

What is claimed:

1. A method for determining the onset and/or monitoring the progression of chronic obstructive pulmonary disease (COPD) in a subject, the method comprising:
   (a) performing Fourier-transform infrared spectroscopy (FTIR) or Variable far infrared radiation spectroscopy (VFIR) spectral analysis of a sputum sample obtained from the subject to produce a spectrum produced from the sample using an FTIR or VFIR machine comprising a processing unit and an output unit;
   (b) wherein said FTIR or VFIR machine processing unit is configured to compare the spectrum produced from the sputum sample obtained from the subject with an FTIR or VFIR spectrum from a normal control produced from a sputum sample obtained from a subject not suffering COPD to determine the onset of COPD in the subject or with an FTIR or VFIR spectrum taken on a sputum sample obtained previously from the subject to determine the progression of COPD in the subject, wherein a difference between the spectrum produced from the sputum sample and the normal control or spectrum taken on the sputum sample obtained previously from the subject at one or more wavenumbers within one or more ranges selected from about 1570 $cm^{-1}$ to about 1590 $cm^{-1}$, and about 1720 $cm^{-1}$ to about 1750 $cm^{-1}$ is indicative that the subject is suffering from COPD or is indicative of the progression of COPD in the subject, respectively; and
   (c) wherein said FTIR or VFIR machine output unit is arranged to provide an output indicative that the subject is suffering from COPD or indicative of the progression of COPD in the subject according to the comparison made by the processing unit in step (b).

2. The method according to claim 1, wherein said difference is an increase or decrease in absorbance at a same wavenumber or a shift in position of absorbance between wavenumbers between sputum spectra within one or more ranges selected from about 1570 $cm^{-1}$ to about 1590 $cm^{-1}$ and about 1735 $cm^{-1}$ to about 1750 $cm^{-1}$.

3. The method according to claim 2 wherein said method additionally comprises comparing the spectrum at wavenumbers within a range from about 1400-1420 $cm^{-1}$.

4. The method according to claim 2 wherein the control is normalised for a population where there is no COPD.

5. The method according to claim 2 wherein said method is undertaken for identifying a risk of flair ups at an early stage or identifying a risk of acute exacerbation of COPD.

6. The method according to claim 1, wherein said difference is an increased absorbance at a wavenumber selected from one or more of about 1570 to about 1590 $cm^{-1}$, and about 1740 $cm^{-1}$ to about 1748 $cm^{-1}$.

7. The method according to claim 6 wherein said method additionally comprises comparing the spectrum at wavenumbers within a range from about 1400-1420 $cm^{-1}$.

8. The method according to claim 6 wherein the control is normalised for a population where there is no COPD.

9. The method according to claim 6 wherein said method is undertaken for identifying a risk of flair ups at an early stage or identifying a risk of acute exacerbation of COPD.

10. The method according to claim 1 wherein said method additionally comprises comparing the spectrum at wavenumbers within a range from about 1400-1420 $cm^{-1}$.

11. The method according to claim 1 wherein the control is normalised for a population where there is no COPD.

12. The method according to claim 1 wherein said method is undertaken for identifying a risk of flair ups at an early stage or for identifying a risk of acute exacerbation of COPD.

* * * * *